ced by examiner

(12) United States Patent
Neffgen et al.

(10) Patent No.: US 8,686,061 B2
(45) Date of Patent: Apr. 1, 2014

(54) MULTICOMPONENT SYSTEM FOR PRODUCING A DENTAL MATERIAL

(75) Inventors: Stephan Neffgen, Pinneberg (DE); Karsten Hauser, Hamburg (DE)

(73) Assignee: Muhlbauer Technology GmbH, Norderfriedrichskoog (DE)

( * ) Notice: Subject to any disclaimer, the term of this patent is extended or adjusted under 35 U.S.C. 154(b) by 0 days.

(21) Appl. No.: 13/516,602

(22) PCT Filed: Dec. 16, 2010

(86) PCT No.: PCT/EP2010/069975
§ 371 (c)(1),
(2), (4) Date: Jun. 15, 2012

(87) PCT Pub. No.: WO2011/083020
PCT Pub. Date: Jul. 14, 2011

(65) Prior Publication Data
US 2012/0259032 A1    Oct. 11, 2012

(30) Foreign Application Priority Data
Dec. 16, 2009   (DE) .................. 10 2009 058 638

(51) Int. Cl.
*A61L 2/08* (2006.01)
*B41M 7/00* (2006.01)
*B29C 71/04* (2006.01)
*C08F 2/46* (2006.01)
*C08G 61/04* (2006.01)

(52) U.S. Cl.
USPC .............. 522/79; 522/74; 522/71; 522/189; 522/1; 520/1

(58) Field of Classification Search
USPC ................. 522/79, 74, 71, 189, 1; 520/1
See application file for complete search history.

(56) References Cited

U.S. PATENT DOCUMENTS

| 4,145,378 A | 3/1979 | Arrighetti et al. |
| 5,688,883 A * | 11/1997 | Klee et al. ............... 526/141 |
| 6,437,065 B1 | 8/2002 | Ritter et al. |
| 6,852,775 B1 * | 2/2005 | Soglowek et al. ............ 523/109 |
| 7,183,334 B2 * | 2/2007 | Guzauskas ................ 522/31 |

FOREIGN PATENT DOCUMENTS

| DE | 19719890 | 11/1998 |
| DE | 19928238 | 12/2000 |
| EP | 0374824 | 6/1990 |
| EP | 0732098 | 9/1996 |
| EP | 1194110 | 4/2002 |
| EP | 1237525 | 9/2002 |
| EP | 1242493 | 10/2003 |
| EP | 2070506 | 6/2009 |
| WO | 00/78271 | 12/2000 |
| WO | 01/43700 | 6/2001 |
| WO | 01/44338 | 6/2001 |
| WO | 2011/083020 | 7/2011 |

OTHER PUBLICATIONS

Bredereck et al., "About CH-active Polymerization initiatiors—XIIIth communication Polymerizations and Polymerization Initiators," Makromol Chem, 1966, 92: 70-90.
Bredereck et al., "Polymerizations and Polymerization 16, Influence of thioxo groups in barbituric acid derivatives on the initiation of polymerization of methyl methacrylate," Mackromol Chem, 1975, 176: 1713-1723.
English Abstract of EP1194110 A1 published Apr. 10, 2002.
English Abstract of EP1237525 published Sep. 11, 2002.
English Translation of the International Preliminary Report on Patentability for Int'l Application No: PCT/EP2010/069975, mailed Jul. 12, 2012.
English Translation of the International Search Report for International Application No. PCT/EP2010/066975, mailed Mar. 23, 2012.
EPO Machine Translation of DE197119890 A1 Description, Published Nov. 19, 1998.
EPO Machine Translation of DE19928238 A1 Description, Published Dec. 28, 2000.
EPO Machine Translation of EP2070506 A1 Description, published Jun. 17, 2009.
International Search Report for International Application No. PCT/EP2010/066975, mailed Mar. 23, 2012.
Fischer et al., "On C-dialkylbarbituric acids and on the ureides of the dialkylacetic acids.," Annal Chemie, 1904, 335:334-368.

* cited by examiner

*Primary Examiner* — Ling Choi
*Assistant Examiner* — Jessica E Whiteley
(74) *Attorney, Agent, or Firm* — Casimir Jones, S.C.

(57) ABSTRACT

The invention relates to a two-component or multicomponent system for producing a dental material, to the use of the system for producing a dental material.

26 Claims, No Drawings

MULTICOMPONENT SYSTEM FOR PRODUCING A DENTAL MATERIAL

The present invention is a §371 National Entry of International Patent Application Serial Number PCT/EP2010/069975, filed Dec. 16, 2010, which is incorporated herein by reference, and which claims priority to German Patent Application Serial Number 102009058638.5, filed Dec. 16, 2009.

The invention relates to a two-component or multicomponent system for producing a dental material in accordance with the preamble of claim 1, to a kit featuring this system, and to the use of the system for producing a dental material.

Polymerizable dental materials of the kind referred to above are known from WO 00/78271 A1, for example, and find use, for example, as filling materials, adhesives, core buildup materials, crown and bridge materials, and also temporary crown and bridge materials, and cements.

For producing dental materials, the components of the system are mixed to a pasty composition and applied. This composition is cured by radical polymerization.

Various initiator systems are described in the prior art for the radical polymerization.

For example, EP 0 374 824 A1 discloses amine-peroxide systems for initiating polymerization. The amines used may be objectionable on grounds of toxicity, and also often lead to esthetically unacceptable discoloration of the restoration material. In certain circumstances, moreover, there may be comparatively high temperatures in the course of curing, which may damage adjacent tooth material such as the pulp, for example.

The object on which the invention is based is that of providing a system of the kind referred to at the outset which can be processed in practice with good results and can be cured, and has a good shelf life.

The invention achieves the object in connection with the systems referred to at the outset in that the first and/or second component comprises at least one peroxide selected from the group consisting of perethers, peracetals, and perketals.

First of all it is appropriate to elucidate a number of terms used in the context of the invention.

The invention provides a two-component or multicomponent system, preferably a two-component system. The dental material, accordingly, is made up from at least two, preferably precisely two, components.

The first component comprises at least one radically polymerizable resin and also a polymerization accelerator, which does not itself act as a polymerization initiator and hence does not, or not significantly, adversely affect the shelf life of the first component. Polymerization accelerators used are preferably, in particular, combinations of divalent transition metal ions and halide or pseudohalide ions, more particularly chloride ions.

The second component comprises as polymerization initiator a CH-acidic compound and/or a salt of a CH-acidic compound.

Corresponding CH-acidic compounds have been investigated very thoroughly by H. Bredereck and his coworkers (H. Bredereck et al.: "Über CH-Aktive Polymerisationsinitiatoren—XIII. Mitt. Polymerisationen und Polymerisationsinitiatoren" [Concerning CH-active polymerization initiators— XIIIth communication Polymerizations and Polymerization Initiators"], die Makromolekulare Chemie 92 [1966] pp. 70-90; H. Bredereck et al.: "Polymerisationen und Polymerisationsinitiatoren—16. Einfluβ von Thio-Gruppen in Barbitursäurederivaten auf die Polymerisationsauslösung von Methacrylsäure-methylester" [Polymerizations and Polymerization Initiators—16. Effect of thio groups in barbituric acid derivatives on the initiation of polymerization of methyl methacrylate"] die Makromolekulare Chemie 176 [1975] pp. 1713-1723). Of the CH-acidic compounds, the barbituric acid derivatives have proven favorable in the dental segment. They can be prepared in high yields and purities, are available industrially (Chemische Fabrik Berg GmbH, Mainthalstr. 3, D-06749 Bitterfeld), and, by virtue of their reaction kinetics, permit the realization of advantageous properties.

The synthesis of the barbituric acid derivatives is known for example from E. Fischer and A. Dilthey: "Über c-Dialkylbarbitursäuren and über die Ureide der Dialkylessigsäuren" [Concerning c-dialkylbarbituric acids and concerning the ureides of the dialkylacetic acids], Ann. 335 [1904] p. 335) and describes the alkaline condensation of derivatives of diethyl malonate with N-substituted urea in sodium alcoholate. The resultant sodium salts of the barbituric acid derivatives are subsequently converted into the barbituric acid derivatives by addition of an acid, such as hydrochloric acid, for example.

In the case of the initiator system based on barbituric acid and/or derivatives thereof, the barbituric acid derivatives must be stored separately from the polymerizable monomers. The reason for this is that CH-acidic compounds such as the derivatives of barbituric acid form hydroperoxides even without the assistance of Cu(II) ions and chloride ions, as a result of autoxidation by atmospheric oxygen. These hydroperoxides undergo decomposition and, in so doing, form radicals which initiate the polymerization of the reactive monomers, meaning that within a short time there is spontaneous polymerization. This spontaneous polymerization process can be retarded or suppressed for a short time by addition of stabilizers, but not over the kind of longer time period desirable in the case of shelf-stable systems.

In one variant of the invention, therefore, a constituent of the second component is an inert matrix which is pasty or liquid at room temperature and which cannot be caused to polymerize by the CH-acidic compound. Suitable examples include plasticizers such as, for example, polyethylene glycols, which are described in more detail below.

In a second variant of the invention, the second component may likewise comprise radically polymerizable resins. The precondition for this is that the CH-acidic compound present in the second component is in the form of a salt. A CH-acidic compound in the form of a salt is not yet able, in this salt form, to act as a polymerization initiator. For that purpose it must first be converted, by means of an acid, for example, into the corresponding CH-acidic compound itself. In this embodiment of the invention, the second component may comprise, for example, a basic compound, which stabilizes the salt of the CH-acidic compound and preferably does not cause decomposition of the peroxide component. The first component may comprise a suitable acid which is capable of protonating the salt of the CH-acidic compound. After the two components have been mixed together, the acid protonates the salt to form the free CH-acidic compound, which then acts as polymerization initiator.

In a further preferred embodiment of the invention, the first component comprises at least one radically polymerizable acid. Suitable radically polymerizable acids are, more particularly, the radically polymerizable resins which can be used as a constituent of the first component in the context of the invention and which comprise acid groups, as for example carboxylic, sulfonic, phosphonic or phosphoric acid groups.

The invention has recognised that the mechanical properties, in particular, of dental materials after curing can be improved substantially over the prior art, which uses CH-acidic compounds and transition metal ions, through the use of peroxides selected from the group consisting of perethers, peracetals, and perketals, the perketals being preferred in accordance with the invention. In accordance with the invention, surprisingly, the shelf life of the as yet uncured components of the system is high, and the mechanical properties of the cured dental material after prolonged storage of the components are good.

In accordance with the invention the peroxide is present preferably in the second component. The amount of the peroxides added in accordance with the invention in the two-component system is preferably 0.001% to 5% by weight, more preferably 0.01% to 3% by weight, more preferably 0.02% to 2% by weight, more preferably 0.02% to 1.5% by weight, more preferably 0.03% to 1% by weight. The stated upper and lower limits can be combined as desired to form ranges according to the invention.

Surprisingly, the components of the dental materials of the invention have particularly good shelf stability and even after prolonged storage the hardening characteristics are consistent and desirable. Mechanical properties such as hardness and more particularly flexural strength/flexural modulus of the cured dental material are unaffected, or affected only insubstantially, by prolonged storage of the components prior to processing and curing.

Among the peroxides used in accordance with the invention (perethers, peracetals, and perketals), those which are employed with preference are those whose 10-hour half-life temperature is at least 75° C., preferably at least 80° C. This means that after storage of the peroxide at this temperature for ten hours, half of the peroxide sample has undergone decomposition. The half-life is the time within which half of the amount of peroxide undergoes decomposition in a particular solvent. The half-lives were determined in 0.1 molar monochlorobenzene.

Suitable perethers are, for example, $R^1(-O-O-R^3)_a-O-O-R^2$, where $R^1$ and $R^2$=optionally substituted alkyl, cycloalkyl, alkylaryl, aryl; $R^3$=alkylene, a preferably between 0 and 4. Preference is given for example to di-tert-amyl peroxide, dicumyl peroxide, di(2-tert-butylperoxyisopropyl)benzene, 2,5-dimethyl-2,5-di(tert-butylperoxy)hexane, tert-butylcumyl peroxide, 2,5-dimethyl-2,5-di(tert-butylperoxy)hex-3-yne or di-tert-butyl peroxide.

Perketals $(R^1_2C(-O-O-R^2)_2)$ and peracetals $(R^1HC(-O-O-R^2)_2)$ are compounds which derive from ketals and acetals, respectively, by formal replacement of the oxygen bridge between the alkyl groups with an oxygen-oxygen bridge (replacement of an oxygen with a peroxo group).

Particularly preferred are the perketals. Suitable perketals are aliphatic or cyclic perketals.

Suitable perketals are, for example, 1,1-di(tert-butyl-peroxy)-3,3,5-trimethylcyclohexane; 1,1-di(tert-butyl-peroxy)cyclohexane; 2,2-di(tert-butylperoxy)butane, 1,1-di(tert-amylperoxy)cyclohexane, butyl 4,4-di-(tert-butylperoxy)valerate, ethyl 3,3-di(tert-amyl-peroxy)butanoate, and ethyl 3,3-di(tert-butylperoxy)butanoate. A preferred cyclic perketal is, for example, 3,6,9-triethyl-3,6,9-trimethyl-1,4,7-triperoxononane.

Suitable CH-acidic compounds are known to the skilled person. Suitable CH-acidic compounds are those which have hydrogen on C atoms in α position to one or, preferably, two or more electron-withdrawing group(s). Examples of suitable CH-acidic compounds are α-benzoylpropionitriles, α-cyanocarboxylic esters and amides, cyclic β-oxonitriles, β-diketones, cyclic β-diketones, cyclic β-oxocarboxylic esters, cyclic β-oxolactones, malonic acids, more particularly malonyl-sulfamide, pyrazoles, more particularly pyrazolone and pyrazolidine, barbituric acid, barbituric acid derivatives, thiobarbituric acid, thiobarbituric acid derivatives, and also the salts, more particularly alkaline earth metal salts and alkali metal salts, and also partly or fully alkylated or arylated or mixedly alkylated or arylated ammonium or phosphonium salts of aforesaid compounds. Other organically modified cations can be used as well. Preference as barbituric acid derivatives is given to 1,3,5-dimethylbarbituric acid, 1,3-dimethyl-5-ethylbarbituric acid, 1,5-dimethyl-barbituric acid, 1-methyl-5-ethylbarbituric acid, 1-methyl-5-propylbarbituric acid, 5-ethylbarbituric acid, 5-propylbarbituric acid, 5-butylbarbituric acid, and 1-cyclohexyl-5-ethylbarbituric acid. With particular preference the barbituric acid derivative is 5-phenyl-1-benzylbarbituric acid (PBS). With particular preference the barbituric acid derivative is phenylbenzylbarbituric acid (PBS).

Ionic halide or pseudohalide compounds are preferably selected such that they possess sufficient solubility in the respective component. Particularly preferred here are ammonium salts, more particularly tetraalkyl-ammonium salts of the kind described in EP 2 070 506 (Lück). Particularly preferred halides are chlorides.

Preferred polymerization accelerators comprise metal compounds which are soluble in the resin system and comprise metal ions capable of a change in oxidation state, such as Cu(II), Fe(II), Fe(III) or Co salts of organic acids or complexes thereof. Particularly preferred are compounds of copper such as Cu(II) sulphate (anhydrous and hydrate forms), $CuCl_2$, copper acetate, copper acetylacetonate, copper naphthenate, copper salicylate, copper complexes with EDTA, bis(1-phenylpentane-1,3-dionato)copper, copper dimethacrylate, and copper benzoylacetonate.

In one preferred embodiment, ionic compound and polymerization accelerator are located together in the first component, comprising the polymerizable resins.

It may be preferable to use additional (non-CH-acidic) reducing agents as a further component of the initiator system. Suitable additional reducing agents are described in EP 0732098, for example. Additionally suitable here are N,N-dialkylated aromatic amines such as N,N-bishydroxyethyl-p-toluidine, or N,N-dialkylated aminobenzoic esters such as ethyl p-N,N-dimethylaminoenzoate. Amine compounds are particularly preferred. The additional reducing agents are present preferably in the first component, which does not contain the peroxide.

The initiator system of the invention may include a photochemically activable initiator system. Preferred are initiator systems which can be activated in the blue light region, such as 1,2-dicarbonyl compounds, examples being camphorquinone-amine systems, and/or, alternatively, those which can be activated in the UV light range, examples being phosphine oxides. The preferred photoinitiators are characterized in that by absorption of light in the wavelength range from 300 nm to 700 nm, preferably from 350 nm to 600 nm, and more preferably from 380 nm to 500 nm, and optionally by the additional reaction with one or more coinitiators, they are able to bring about the curing of the material. Preference here is given to using phosphine oxides, bezoin ethers, benzyl ketals, acetophenones, benzophenones, thioxanthones, bisimidazoles, metallocenes, fluorones, α-dicarbonyl compounds, aryldiazonium salts, arylsulfonium salts, aryliodonium salts, ferrocenium salts, phenylphosphonium salts or a mixture of these compounds.

Particular preference is given to using diphenyl-2,4,6-trimethylbenzoylphosphine oxide, benzoin, benzoin alkyl ethers, benzyl dialkyl ketals, α-hydroxyacetophenone, dialkoxyacetophenones, α-aminoacetophenones, isopropylthioxanthone, camphorquinone, phenylpropanedione, 5,7- diiodo-3-butoxy-6-fluorone, (eta-6-cumene) (eta-5-cyclopentadienyl)iron hexafluorophosphate, (eta-6-cumene)(eta-5-cyclopentadienyl)iron tetrafluoroborate, (eta-6-cumene) (eta-5-cyclopentadienyl)iron hexafluoroantimonate, substituted diaryliodonium salts, triarylsulfonium salts or a mixture of these compounds.

Coinitiators used for photochemical curing are preferably tertiary amines, borates, organic phosphites, diaryliodonium compounds, thioxanthones, xanthenes, fluorenes, fluorones, α-dicarbonyl compounds, fused polyaromatics or a mixture of these compounds. Particular preference is given to using N,N-dimethyl-p-toluolidine, N,N-dialkyl-alkyl-anilines, N,N-dihydroxyethyl-p-toluidine, 2-ethylhexyl p-(dimethylamino)benzoate, butyrylcholine triphenylbutyl-borate or a mixture of these compounds.

Resins are preferably the customary dental (meth)acrylates, di(meth)acrylates and/or more highly functionalized (meth)acrylates that are known to the skilled person. Without restricting the generality, a number of examples are stated below: methyl(meth)acrylate, ethyl(meth)acrylate, n- or isopropyl(meth)acrylate, n-, iso- or tert-butyl(meth)acrylate, hexyl(meth)acrylate, 2-ethylhexyl(meth)acrylate, cyclohexyl(meth) acrylate, isobornyl(meth)acrylate, hydroxyethyl (meth)acrylate, hydroxypropyl(meth)acrylate, phosphoric esters of hydroxyethyl(meth)acrylate and/or hydroxypropyl (meth)acrylate, (meth)acrylic acid, malonic acid mono(meth) acrylate esters, succinic acid mono(meth)acrylate esters, maleic acid mono(meth)acrylate esters, glycerol(meth)acrylate, glycerol(meth)acrylate esters, glycerol di(meth)acrylate, glycerol di(meth)acrylate esters (such as, for example, glycerol di(meth)acrylate succinate), 4-(meth)acryloyloxyethyltrimellitic acid, bis-4,6- and bis-2,5-(meth)acryloyloxyethyltrimellitic acid, 2-(((alkylamino)carbonyl)oxy)ethyl (meth)acrylates, allyl(meth)acrylate, tetrahydrofurfuryl (meth)acrylate, butanediol di(meth)acrylate, hexanediol di(meth)acrylate, decanediol di(meth)acrylate, dodecanediol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylates, glycerol di(meth)acrylate, glycerol propoxytri(meth)acrylate, trimethylolpropane tri(meth)acrylate, ethoxylated and/or propoxylated trimethylolpropane tri (meth)acrylates, pentaerythritol tri(meth)acrylate, pentaerythritol tetra(meth)acrylate, dipentaerythritol penta (meth)acrylate, dipentaerythritol hexa(meth)acrylate, bisphenol A di(meth)acrylate, ethoxylated and/or propoxylated bisphenol A di(meth)acrylates, 2,2-bis-4-(3-(meth) acryloyloxy-2-hydroxypropoxy)phenylpropane and compounds derived therefrom, chloro- and bromophosphoric esters of bisphenol A glycidyl(meth)acrylate, urethane(meth) acrylates such as, for example, 7,7,9-trimethyl-4,13-dioxo-3, 14-dioxa-5,12-diazahexadecane 1,16-dioxydimethacrylate, oligomeric or polymeric urethane(meth)acrylates having a functionality of two or more, of the kind described in EP 1237525 or in EP 1242493, for example, polyester(meth) acrylates, polycarbonate(meth)acrylates, polyamide(meth) acrylates, polyimide(meth)acrylates, phosphazene(meth) acrylates and siloxane(meth)acrylates.

However, other radically polymerizable systems as well are possible. The monomers may be neutral, basic or acidic. The monomer molecules may contain any of a very wide variety of functionalities, such as hydroxyl functions, amino functions, carboxyl functions, and also other customary organic functionalities. Likewise present preferably may be the dimethacrylates with tricyclodecane core structures that are described in EP 2016931.

Suitable plasticizers are known to the skilled person. They include, for example, polyethylene glycols, polypropylene glycols, unsaturated and saturated polyesters, phthalates, adipates, sebacates, phosphoric esters, phosphonic esters and/or citric esters. Examples of particularly suitable plasticizers are polyethylene glycol derivatives such as polyethylene oxide, 2,2-bis[4-[oligo(ethoxy)]phenyl]propane diacetate, 2,2-bis [4-[2-hydroxyethoxy]phenyl]propane diacetate, polypropylene glycol derivatives, other polyethers and oligoethers, low molecular mass polyesters, phthalic esters, silicone oils, liquid paraffins, and the like.

One or both components of the two-component system of the invention preferably further comprise customary dental additives, examples being additives selected from the group consisting of fillers and thixotropic agents.

The system of the invention may comprise fillers in at least one of the components. The fillers used in accordance with the invention are preferably nanoscale and/or microscale (in some cases X-ray-opaque) fillers, preferably glass powders, glass-ceramic powders, metal oxides, semimetal oxides or mixed metal oxides, silicate, nitride, sulphate, titanate, zirconate, stannate, tungstate, silicon dioxide compounds, or a mixture of these compounds, or spherical fillers, quartz powders, β-cristobalite, X-ray-opaque dental glasses or a mixture of these powders, or filled or unfilled chip polymers and/or bead polymers.

The nanoscale fillers used in accordance with the invention are, with particular preference, silicon dioxide, aluminum oxide, zirconium dioxide, titanium dioxide, zinc oxide, tin dioxide, cerium oxide, aluminum silicon oxides, silicon zinc oxides, silicon zirconium oxides, iron oxides and mixtures thereof with silicon dioxide, indium oxides and mixtures thereof with silicon dioxide and/or tin dioxide, boron nitride, strontium sulfate, barium sulfate, strontium titanate, barium titanate, sodium zirconate, potassium zirconate, magnesium zirconate, calcium zirconate, strontium zirconate, barium zirconate, sodium tungstate, potassium tungstate, magnesium tungstate, calcium tungstate, strontium tungstate and/or barium tungstate.

In accordance with one preferred embodiment of the invention, the filler may be a surface-modified filler, preferably an organically surface-modified filler. Following its surface modification, such as a silanization, for example, the filler may possess on its surface functional groups, as for example reactive methacrylate groups, which are able to react chemically, preferably radically, with the monomers or which have a high affinity to the polymer matrix formed from the monomers.

For the establishment of particular properties, the system of the invention may further comprise what are called additives or modifiers. Without restriction on the generality, a number of examples are given below: inorganic and/or organic color pigments or dyes, fluorescent dyes for attaining the natural fluorescence of the tooth, stabilizers (such as, for example, substituted and unsubstituted hydroxyaromatic compounds, Tinuvins, terpinene, phenothiazine, stabilizers of HALS type (Hindered Amine Light Stabilizers—and/or heavy-metal scavengers such as EDTA), ion donor substances, more particularly those which release fluoride ions (such as, for example, sodium fluoride, potassium fluoride, yttrium fluoride, ytterbium fluoride and/or quaternary ammonium fluorides), bactericidal or antibiotic substances (such as, for example, chlorhexidine, pyridinium salts, penicillins, tetracyclines, chloramphenicol, antibacterial macrolides and/or polypeptide antibiotics) and/or solvents (such as, for example, water, acetone, ethanol, isopropanol, butanone and/ or ethyl acetate), flavors, and fragrances.

As well as the addition of customary dental additives known to the skilled person, it may be advantageous to use dryers for the absorption of water as constituents. Examples of suitable dryers include zeolites, anhydrous or dewatered salts such as $MgSO_4$ or $CaSO_4$ hemihydrate, dried silica gel, $CaCl_2$, and silica gels. Particularly preferred is the use of a dryer in the component which comprises the peroxide.

The components take the form of liquids, preferably of (flowable) pastes. Production is accomplished by suitably mixing the constituents of the individual components by means of suitable methods such as stirring, kneading, dispersing, rolling, etc. until homogeneous components are obtained.

For hardening, the components of the material are mixed with one another by hand or, preferably, automatically by means of static or dynamic mixers (for example, MixPac® from Sulzer). Optionally it is possible for further components to be admixed.

The components may comprise acidic constituents, such as polymerizable acids or else nonpolymerizable acids. Weak, moderately strong or else strong acids may be suitable here. In one specific embodiment, the component which does not comprise the peroxide comprises hydroxyl-functional compounds and/or water. An optional acid, preferably a moderately strong to strong acid, may then be present additionally in one of the two, or in both, components.

The two-component or multicomponent system of the invention can be used for producing a dental material. The dental material produced is preferably selected from the group consisting of filling materials, adhesives, core buildup materials, crown and bridge materials, temporary crown and bridge materials, and also cements.

The invention further provides a kit for producing a dental material, which comprises a two-component or multicomponent system of the invention in suitable containers. These may be suitable holding containers, cartridges for static or dynamic mixers or the like. A suitable mixing means may be a constituent of the kit, such as an abovementioned static or dynamic mixer.

Working examples of the invention are described below. The following constituents available commercially were employed:

| | |
|---|---|
| BisGMA | Bisphenol A diglycidyl dimethacrylate (CAS 001565-94-2) |
| TEDMA | triethylene glycol dimethacrylate |
| UDMA | 7,7,9-trimethyl-4,13-dioxo-3,14-dioxa-5,12-diazahexadecane-1,16-dimethacrylate (CAS 72869-86-4) |
| BPA(EO)$_4$DMA | 2,2-bis[4-[oligo(ethoxy)]phenyl]-propane dimethacrylate (average of 4 ethoxy units per molecule) |
| HEMA | 2-hydroxyethyl methacrylate |
| BTBAC1 | benzyltributylammonium chloride |
| CuDMA | copper dimethacrylate |
| BHT | 2,6-di-tert-butyl-4-methylphenol |
| PBS | phenylbenzylbarbituric acid |
| PK (perketal) | 2,2-di(tert-butylperoxy)butane (approximately 50% strength solution in isododecane) |
| BPO (diacyl peroxide) | dibenzoyl peroxide |
| CU (hydroperoxide) | cumene hydroperoxide |
| AEC percarbonate | tert-amyl peroxy-2-ethylhexyl carbonate |
| R812S | Aerosil ® R812S (Degussa) |
| barium glass, MEMO-sil. | barium glass in $d_{50}$ = 1.5 μm grind, silanized with 3.8% by weight 3-methacryloylpropyltrimethoxysilane |
| barium glass, vinyl-sil | barium glass in $d_{50}$ = 1.5 μm grind, silanized with 3.0% by weight triethoxyvinylsilane |
| PEG 400 | polyethylene glycol, MW 400 |

Test Methods

Unless otherwise indicated, all tests were carried out at a temperature of 23±1° C.

Flexural Strength/Flexural Modulus

The paste components of the paste combinations for measurement are introduced air-free into the chambers of a 10 ml twin safety cartridge (from Sulzer MixPac) with a mixing ratio of the components of 10:1. In accordance with ISO 4049, 5-6 test specimens per combination of materials are produced from this system by automatic mixing (green mixing needle MLX 3.2-12-S 10:1 from Sulzer Mixpac), and are stored and subjected to measurement. The average values and standard deviations are indicated in the results tables in each case.

Hardening Time

The ultimate hardening time (UHT) of the automatically mixed pastes was determined in a rheometer with coaxial cylinders. For this purpose, an approximately constant amount of each paste was applied to a lower plastics cylinder. 30 seconds after the beginning of mixing, a top, hollow metal cylinder conditioned permanently to a temperature of 37° C. was pressed into the paste until it reached a defined distance from the lower cylinder. The two cylinders were oscillated relative to one another, and the force required to achieve this was recorded by means of a plotter. The ultimate hardening time was the time from which the recorded force remained constant.

Gel Time

The material is mixed automatically within a few seconds from the twin safety cartridge and is applied to a mixing block. The paste is subsequently circulated continuously at intervals of a few seconds. When the gelling of the paste mixture has reached an advanced state in which there is perceptible elasticity and at which homogeneous mixing is no longer possible, the gel time point has been reached. The time reported is that from the end of the automatic mixing operation until the gel time point.

Barcol Hardness

The material is applied from the twin safety cartridge with mixing needle within a few seconds into a cylindrical stainless steel mold having a height of 2.5±0.1 mm and a diameter of 25±0.1 mm and is left to cure. The test specimens obtained in this way were stored in water at 37° C. for about 24 hours. The test specimens were removed and the Barcol hardness was determined by means of a Barber-Colman impressor. In each case 5 values, distributed over a test specimen, are determined, and the average of these values is formed.

PREPARATION EXAMPLE 1

(BTBAC1) Solution 10 parts by weight of BTBAC1 are stirred using a magnetic stirrer in 90 parts by weight of HEMA until the solution is homogeneous.

PREPARATION EXAMPLE 2

(CuDMA) Solution 2 parts by weight of CuDMA are stirred using a magnetic stirrer in 98 parts by weight of HEMA until the solution is clear.

INVENTIVE AND REFERENCE EXAMPLES (COMPARATIVE EXAMPLES)

First of all, the liquid components, the solutions from the preparation examples, and, where present in the formula, peroxides are weighed out into a glass vessel, to give the proportions indicated in the tables below. The mixtures thus prepared are stirred using an overhead stirrer until the solution is clear.

The respective resin mixtures are transferred quantitatively into a laboratory mixer. R812S and silanized barium glass are stirred until the distribution of the fillers in the mixture is homogeneous. The pastes prepared in this way are rolled using a triple-roll mill (from Exakt) and then degassed under reduced pressure. The pastes are investigated in pairs in each case within an example, as indicated in the tables. All quantity figures are given in parts by weight.

Compositions

Peroxide in the Second Component (Plasticizer Component)

Second Component (Plasticizer Component)

|  | Ref. 1 | Ref. 2 | Ref. 3 | Ref. 4 | Ref. 5 | Inv. Ex. 1 |
|---|---|---|---|---|---|---|
| PEG 400 | 44.0 | 44.0 | 43.35 | 44.78 | 44.46 | 41.0 |
| Barium glass vinyl-sil. | 50.0 | 50.0 | 49.2 | 49.2 | 49.2 | 50.0 |
| Aerosil R812-S | 3.0 | 3.0 | 2.9 | 2.9 | 2.9 | 3.0 |
| PBS | 3.0 | — | 3.0 | 3.0 | 3.0 | 3.0 |
| PK | — | 3.0 | — | — | — | 3.0 |
| HX | — | — | — | — | — | — |
| BPO | — | — | 1.55 | — | — | — |
| CU | — | — | — | 0.12 | — | — |
| AEC | — | — | — | — | 0.44 | — |

First Component (Resin Component) for Ref. 1-5 and Inv. Ex. 1

| Bis-GMA | 7.188 |
|---|---|
| UDMA | 13.92 |
| TEDMA | 2.085 |
| BPA(EO)$_4$DMA | 23.2 |
| HEMA | 0.548 |
| BHT | 0.007 |
| Cu-DMA | 0.002 |
| BTBACl | 0.05 |
| Barium glass | 50.0 |
| MEMO-sil. | |
| Aerosil R812-S | 3.0 |

Peroxide in First Component (Resin Component)

Example 2

Second Component (Plasticizer Component)

| PEG 400 | 44.0 |
|---|---|
| Barium glass vinyl-sil. | 48.5 |
| Aerosil R812-S | 3.0 |
| PBS | 3.0 |
| BTBACl | 1.5 |

First Component (Resin Component)

| Bis-GMA | 7.266 |
|---|---|
| UDMA | 14.07 |
| TEDMA | 2.107 |
| BPA(EO)$_4$DMA | 23.45 |
| HEMA | 0.098 |
| BHT | 0.007 |
| Cu-DMA | 0.002 |
| Barium glass MEMO-Sil. | 49.0 |
| Aerosil R812-S | 3.0 |
| PK | 1.0 |

Properties

|  | Ref. 1 | Ref. 2 | Ref. 3 | Ref. 4 | Ref. 5 | Inv. Ex. 1 | Inv. Ex. 2 |
|---|---|---|---|---|---|---|---|
| Gel time[s] start | 120 | No curing after 40 h | 69 | 37 | 74 | 90 | 112 |
| 4 wks 40° C. | 125 | | no curing | 103 | 140 | 120 | 128 |
| UHT[s] start | 570 | | 636 | 168 | 219 | 450 | 462 |
| 4 wks 40° C. | 294 | | no curing | 297 | 348 | 282 | 378 |
| FS [MPa] start | 15 ± 1 | | 11 ± 1 | 75 ± 5 | 86 ± 7 | 50 ± 2 | 50 ± 4 |
| 4 wks 40° C. | 30 ± 2 | | no curing | 38 ± 4 | 33 ± 3 | 53 ± 5 | 68 ± 6 |
| FM [GPa] start | 0.39 ± 0.04 | | 0.24 ± 0.05 | 2.8 ± 0.1 | 3.2 ± 0.3 | 1.4 ± 0.1 | 1.4 ± 0.1 |
| 4 wks 40° C. | 1.0 ± 0.1 | | no curing | 1.3 ± 0.1 | 1.1 ± 0.2 | 2.0 ± 0.3 | 2.4 ± 0.2 |
| Barcol hardness 24 h start | 14 | | 14 | 54 | 55 | 44 | 42 |
| 4 wks 40° C. | 34 | | no curing | 41 | 41 | 53 | 52 |

It is found that inventive examples 1 and 2, which comprise barbituric acid and the perketal of the invention, exhibit mechanical properties which are stable and improve significantly over the peroxide-free system (ref. 1) even after a storage time of 4 weeks at 40° C.

The markedly improved mechanical properties found initially when using the percarbonate (AEC, ref. 5, EP 1 194 110 Soglowek) deteriorate markedly after the components have been stored prior to their processing, despite the fact that the material continues to exhibit a satisfactory hardening according to measurement of the hardening time. Compositions of this type apparently do not exhibit sufficient stabilities in relation to these mechanical properties. In view of the decidedly high thermal stabilities of AEC ($T_{1/2}$(10 h)=95° C.), this is not a predictable effect (for comparison PK: $T_{1/2}$ (10 h)=98° C.; both peroxides, therefore, decompose thermally at a similar rate).

The mechanical properties of the cured material, similarly to the case with the percarbonate, are unstable over the storage time of the pastes in the case of the hydroperoxide (CU, ref. 4), and are reduced markedly after 4 weeks at 40° C.

The diacyl peroxide (BPO, ref. 3) shows no positive effect at all with regard to the mechanical properties of the hardened material, and, furthermore, undergoes complete deactivation during storage of the uncured pastes.

Ref. 2, lastly, shows that the initiator systems are geared to the presence of the CH-acidic compound (PBS, barbituric acid), since otherwise hardening does not occur.

The invention claimed is:

1. A two-component or multicomponent system for producing a dental material, comprising:
   a) a first component, comprising:
      i) at least one radically polymerizable resin,
      ii) at least one polymerization accelerator;
   b) a second component, comprising:
      iii) an inert matrix which is pasty or liquid at room temperature, and/or at least one radically polymerizable resin,
      iv) at least one CH-acidic compound and/or a salt of a CH-acidic compound, as polymerization initiator,
   wherein the second component comprises at least one radically polymerizable resin only when the polymerization initiator according to iv) is a salt of a CH-acidic compound,
   wherein the first and/or second component comprises at least one peroxide selected from the group consisting of perethers, peracetals, and perketals.

2. The system of claim 1, wherein said system comprises 0.001% to 5% by weight of said at least one peroxide.

3. The system claim 1, wherein said system comprises 0.01% to 3% by weight of said at least one peroxide.

4. The system of claim 1, wherein said system comprises 0.02% to 2% by weight of said at least one peroxide.

5. The system of claim 1, wherein said system comprises 0.02% to 1.5% by weight of said at least one peroxide.

6. The system of claim 1, wherein said system comprises 0.03% to 1.0% by weight of said at least one peroxide.

7. The system of claim 1, wherein said peroxide is present in said second component.

8. The system of claim 1, wherein said system comprises at least one perketal.

9. The system of claim 1, wherein the 10 h half-life temperature ($T_{1/2}$(10 h)) of said at least one peroxide is at least 75° C.

10. The system of claim 1, wherein the 10 h half-life temperature ($T_{1/2}$(10 h)) of said at least one peroxide is at least 80° C.

11. The system of claim 1, wherein said CH-acidic compound is selected from the group consisting of α-benzoylpropionitriles, α-cyanocarboxylic esters and amides, cyclic β-oxonitriles, β-diketones, cyclic β-diketones, cyclic β-oxocarboxylic esters, and cyclic β-oxolactones, and malonic acids, malonylsulfamide, pyrazoles, pyrazolone, pyrazolidine, barbituric acids, barbituric acid derivatives, thiobarbituric acids, thiobarbituric acid derivatives, and salts thereof.

12. The system of claim 11, wherein said salts of said CH-acidic compounds are selected from the group consisting of alkaline earth metal salts and alkali metal salts.

13. The system of claim 11, wherein said salts of said CH-acidic compounds are selected from the group consisting of partly or fully alkylated or arylated or mixedly alkylated or arylated ammonium or phosphonium salts.

14. The system of claim 1, wherein said polymerization accelerator comprises metal compounds that are soluble in the resin and that comprise transition metal ions capable of a change in oxidation state.

15. The system of claim 1, wherein said system further comprises ionic compounds.

16. The system of claim 15, wherein said ionic compounds comprise ionic halide and/or pseudohalide compounds.

17. The system of claim 15, wherein said ionic compounds are present in said first component.

18. The system of claim 1, wherein said system further comprises a photoinitiator system.

19. The system of claim 1, wherein said radically polymerizable resin comprises (meth)acrylates, di(meth)acrylates and/or more highly functionalized (meth)acrylates.

20. The system of claim 1, wherein said inert matrix comprises plasticizers.

21. The system of claim 20, wherein said plasticizers comprise one or more of polyethylene glycol derivatives, polyethylene oxide, 2,2-bis[4-[oligo(ethoxy)]-phenyl]propane diacetate, 2,2-bis[4-[2-hydroxyethoxy]phenyl]propane diacetate; polypropylene glycol derivatives; other polyethers and oligoethers; polyesters; phthalic esters; silicone oils; or liquid paraffins.

22. The system of claim 1, wherein said system further comprises dental additives selected from the group consisting of fillers, thixotropic agents, pigments, dryers, fluorescent dyes, active antibacterial ingredients, fluorides, and stabilizers.

23. A process for producing dental material, comprising:
   a) providing a two component or multicomponent system comprising;
      1) a first component, comprising:
         i) at least one radically polymerizable resin, and
         ii) at least one polymerization accelerator;
      2) a second component, comprising:
         iii) an inert matrix which is pasty or liquid at room temperature, and/or at least one radically polymerizable resin, and
         iv) at least one CH-acidic compound and/or a salt of a CH-acidic compound, as polymerization initiator,
      wherein the second component comprises at least one radically polymerizable resin only when the polymerization initiator according to iv) is a salt of a CH-acidic compound and wherein said first and/or said second component comprises at least one peroxide selected from the group consisting of perethers, peracetals, and perketals; and
   b) combining said first component and said second component to produce a dental material.

24. The process of claim 23, wherein said dental material is selected from the group consisting of filling materials, adhesives, core buildup materials, crown and bridge materials, temporary crown and bridge materials, and cements.

25. A kit for producing a dental material, comprising a two-component or multicomponent system of claim 1 in containers.

26. The kit of claim 25, further comprising a mixing means.

\* \* \* \* \*